(12) United States Patent
Dong

(10) Patent No.: US 7,250,182 B2
(45) Date of Patent: *Jul. 31, 2007

(54) MEDICAMENT CONTAINING EPIMEDIUM EXTRACT FOR TREATMENT OF PROSTATIC HYPERPLASIA AND PROSTATITIS

(75) Inventor: Hui Dong, Hong Kong (CN)

(73) Assignee: Bright Future Pharmaceutical Laboratories Limited, Yuen Long, N.T., Hong Kong (CN)

( * ) Notice: Subject to any disclaimer, the term of this patent is extended or adjusted under 35 U.S.C. 154(b) by 0 days.

This patent is subject to a terminal disclaimer.

(21) Appl. No.: 11/476,458

(22) Filed: Jun. 28, 2006

(65) Prior Publication Data

US 2006/0246164 A1    Nov. 2, 2006

Related U.S. Application Data

(62) Division of application No. 10/539,497, filed as application No. PCT/CN03/00994 on Nov. 24, 2003.

(30) Foreign Application Priority Data

Dec. 18, 2002    (CN) ................................ 02 1 48571

(51) Int. Cl.
  *A61K 36/25*    (2006.01)
  *A61K 36/00*    (2006.01)
(52) U.S. Cl. ...................................... 424/728; 424/725
(58) Field of Classification Search ...................... None
  See application file for complete search history.

(56) References Cited

U.S. PATENT DOCUMENTS 5,587,167 A * 12/1996 Choi et al. .................. 424/728
5,736,144 A *  4/1998 Gideon ....................... 424/774

FOREIGN PATENT DOCUMENTS

| CN | 1093600 |   | 10/1994 |
| CN | 1113802 |   | 12/1995 |
| CN | 1113802 A | * | 12/1995 |
| CN | 1194862 |   | 10/1998 |
| CN | 1321471 A | * | 11/2001 |
| WO | WO 03/040134 |  | 5/2003 |

* cited by examiner

*Primary Examiner*—Christopher R. Tate
*Assistant Examiner*—Melenie McCormick
(74) *Attorney, Agent, or Firm*—Hudak, Shunk & Farine Co. LPA

(57) ABSTRACT

This present invention relates to a method for extracting *Epimedium* herb to prepare flavones and polysaccharides combinations in which their ratios vary from 2:8 to 8:2 by weight and applying these extracted compositions in treatment of prostatic hyperplasia. Total flavones of the extracts are in the range of 20-90% and the molecular weights of extracted polysaccharides vary from 1,000 to 700,000 Daltons. This invention also includes a method for preparing compounded formulations which contain extracts of Radix Ginseng, pollens, Radix *Astragali*, Cortex *Phellodendri*, *Epimedium* flavones and polysaccharides and administering these compositions directed at treatment of prostatic hyperplasia and prostatitis. Clinical study has showed that these extracts and formulations are effective in treatment of prostate illness with no adverse reactions.

6 Claims, No Drawings

MEDICAMENT CONTAINING *EPIMEDIUM* EXTRACT FOR TREATMENT OF PROSTATIC HYPERPLASIA AND PROSTATITIS

CROSS-REFERENCE

This is a division of application Ser. No. 10/539,497, filed on Jun. 17, 2005, of Hui Dong, for MEDICAMENT CONTAINING EPIDEMIUM EXTRACT FOR TREATMENT OF PROSTATIC HYPERPLASIA AND PROSTATITS, which claims priority to International Application PCT/CN03/00994 filed Nov. 24, 2003 and Chinese Application No. 02148571.2, filed Dec. 18, 2002.

TECHNIQUE

Presented in this application are *Epimedium* herbal compositions and methods that provide a treatment for prostatic hyperplasia. By adjusting the composition of *Epimedium* flavones and polysaccharides and combining *Epimedium* extracts with vehicles or extracts from other Chinese medicinal materials enables development of innovative approach in treatment of prostatic hyperplasia and prostatitis.

BACKGROUND

*Epimedium* Herb is the dried aerial part of *Epimedium brevicornum, Epimedium sagittatum, Epimedium pubescens, Epimedium wushanense* or *Epimedium koreanum*. Its actions are to reinforce the kidney yang, to strengthen the tendons and bones, and to relieve rheumatic condition. It is effective against impotence, seminal emission, weakness of the limbs; rheumatic or rheumatoid arthralgia with numbness and muscle contracture; climacteric hypertension. *Epimedium* Herb consists of flavones, polysaccharides, flavonolignans and alkaloids. Clinical application and pharmacological study of *Epimedium* flavones or polysaccharides showed that they are effective in treating cardiovascular diseases, augmenting the immune system, improving sexual satisfaction, treating osteoporosis and resisting aging. However, all these studies have been done only on either flavones or polysaccharides of Herba *Epimedium*.

INVENTION

This invention provides a technological solution to extract the effective portion of *Epimedium* herbs. These extracts can be used either alone or with vehicles and/extracts from other Chinese medicinal materials in the treatment of prostatic hyperplasia and prostatitis. These regimens are safe, effective and suitable for chronic treatment and geriatric uses.

The extraction relates to a method for extracting the following composition:

A pharmaceutical composition of *Epimedium* extracts comprise flavones and polysaccharides in ratios varied from 2:8 to 8:2 by weight which are used in the treatment of prostatic hyperplasia. Total flavones of the extracts are in the range of 20-90% and the molecular weights of extracted polysaccharides vary from 1,000 to 700,000 Daltons.

The ratios of flavones and polysaccharides can be adjusted to a range of 3:7 to 6:4 by weight of the composition. Total flavones comprise 10-90% of icariin and icariin I, and the molecular weights of extracted polysaccharides vary from 45,000 to 620,000 Daltons.

The method of extracting *Epimedium* herb comprises:

Extract *Epimedium* herb with 60-95% organic solvent. Recover the organic solvent from the filtrate. Add onto the Absorptive Resin ($D_{101}$, or $D_{140}$) Column, and then wash the column with water. Elute the column with 30-85% ethanol and remove the eluent by suction filtration. Collect all the eluent and evaporate to dryness. Total flavones in the residue are about 20-90%.

Decoct the *Epimedium* residue with water and concentrate the aqueous solution. Add ethanol to a concentration of 70-85% and stand still for a while. Filter to obtain the crude polysaccharides. Dissolve the polysaccharides in water and add chloroform n-butanol mixture (3-6: 1) to precipitate protein debris. Remove any polysaccharides below 1000 Daltons by ultra filtration. Concentrate the aqueous extract to dryness and obtain polysaccharides of molecular weight 1,000 to 700,000 Daltons.

Mix the extracted *Epimedium* flavones and polysaccharides to obtain combinations in ratios from 2:8 to 8:2 by weight of composition.

Repeat the *Epimedium* extracting procedure as described with 60-85% organic solvent containing ethanol, propanone, isopropyl alcohol and/or methanol. The ratio of flavones and polysaccharides should fall within a range of 3:7 to 6:4.

Following the *Epimedium* extraction procedure described, the total flavones extract comprises 10-90% *Epimedium* icariin and icariin I. Following the *Epimedium* polysaccharides extraction protocol, the crude polysaccharides is redissolved in water. Add sufficient quantity of ethanol to make up the final concentration of 70-85%. Stand still for a while and harvest the refined polysaccharides by filtration. The molecular weight of polysaccharides lies within 45,000 to 620,000 Daltons.

The Epimedium flavones and polysaccharides can be combined in ratios of 3:7, 4:6, 5:5, 6:4 or 7:3. These combinations can be used alone or with any pharmaceutically acceptable vehicle/excipients.

A pharmaceutical composition of compounded formulations used in treatment of prostatic hyperplasia and prostatitis comprises radix ginseng, pollens, radix astragali, cortex phellodendri, *Epimedium* flavones and/or *Epimedium* polysaccharides.

The composition of these formulations wherein comprise by weight: (1) 1-6 portion of ginseng extract containing 6-10% ginsenoside; (2) 1-8 portion of pollen/pollen extract containing 10-20% flavones; (3) 1-4 portion of radix *astragali* extract containing 3-5% astragaloside and 20-30% polysaccharides; (4) 1-6 portion of cortex phellodendri extract containing 10-15% berberine; (5) 4 -16 portion of *Epimedium* flavones containing 20-90% flavones and/or *Epimedium* polysaccharides.

The composition of above formulation wherein comprises 1-2 portion by weight of ginseng extract, 2-4 portions by weight of pollen or pollen extract, 1-2 portion of by weight radix *astragali* extract, 1-2 portion by weight of cortex *phellodendri* extract and 5-10 portions by weight of *Epimedium* flavones and/or *Epimedium* polysaccharides.

All the discussed formulations can be mixed with any pharmaceutically acceptable vehicle/excipients to formulate various preparations in different dosage forms.

The detail *Epimedium* extracting procedure is as follow:

Extract *Epimedium* leaf powder with 60-95% organic solvent 1-4. times and not exceeding 6-10 ml/g each time. The total extraction time is 1-3 hours. Filter the extract by a suction filtration and add onto a resin column ($D_{101}$ or $D_{140}$). Wash the resin column with water thoroughly, and then elute the column with 30-85% ethanol. Collect all the eluent, recover ethanol by suction filtration and dry to crude flavones (A). The crude extract (A) contains 20-90% flavones and 10-90% icariin and icariin I.

Decoct the *Epimedium* residue with water 3 times and not exceeding 6-10 ml/g each time. The total extraction time is 1-2 hours. Collect the solution by suction filtration and then concentrate the extract. Add ethanol to a concentration of 70-85%. Mix the solution thoroughly and stand still for 12-24 hours. Filter to obtain the precipitate. This precipitation procedure can be repeated 3 times if necessary to obtain the reddish brown polysaccharides. Dissolve polysaccharides in 500 ml of water and add 100-200 ml chloroform n-butanol mixture (3-6:1) to precipitate protein debris. Remove any polysaccharides below 1000 Daltons by ultra filtration. Concentrate the aqueous extract to complete dryness to obtain refined *Epimedium* polysaccharides (B) with Molecular Weight of 1,000 to 700,000. The polysaccharides undergo routine testing and two fractions are identified—extracellular polymer substances 1 (EPS-1) and extracellular polymer substances 2 (EPS-2) with their respective molecular weights of 45000 and 620000. The composition of both EPSs is fucose, rhamnose, pentosidine, xylitose, mannitose, glucose and galactose. Furthermore, we have identified four groups of polysaccharides with their respective molecular weights of 3400, 25000, 45000 and 520000.

The *Epimedium* extracts contain designed portion of crude flavones (A) and refined polysaccharides (B). Experiments demonstrated that the effective ratios of A and B mixtures in treating prostatic hyperplasia are 2:8, 3:7, 4:6, 5:5, 6:4, 7:3 and 8:2.

Clinical research showed that this novel mixing of *Epimedium* flavones and *Epimedium* polysaccharides in designed portion is effective in the management of benign prostatic hyperplasia with a success rate of 93.8%. This patient group's symptomatic score decreases significantly ($P<0.01$) and their quality of life improves prominently, which can be seen from the reduced frequency in nocturnal urination and improvement in urine flow. The rate of urine flow increases substantially ($P<0.01$), which implies a decrease in bladder obstruction. Moreover, the urine retention is decreased ($P<0.01$). The level of Prostate Specific Antigen (PSA) decreased after treatment from a value of 3.31±3.68 ug/L (before treatment) to 3.03±3.84 ug/L (after treatment), but this result is not statistically significant.

Clinical research also showed that the formulation of *Epimedium* extract, pollen or pollen extract, Radix *Astragali* extract, Cortex *Phellodendri* extract and ginseng extract is effective in treating patients with benign prostatic hyperplasia associated with chronic prostatitis and its success rate is 75%. This patient group's symptomatic score decreases significantly ($P<0.01$) and their quality of life improves prominently, which can be seen from the reduced frequency in nocturnal urination and improvement in urine flow. The rate of urine flow increases substantially ($P<0.01$), which implies a decrease in bladder obstruction. Moreover, the urine retention is decreased ($P<0.01$). The level of PSA decreases significantly after treatment from a value of 4.41±5.28 ug/L (before treatment) to 1.84±1.07 ug/L (after treatment), with a P value $<0.01$.

This invention provides a simple procedure to prepare *Epimedium* extract. The extract contains well-defined active components. Taking advantage of the synergistic effect between flavones and polysaccharides, the success rate in treating benign prostatic hyperplasia can be greatly improved by adjusting the ratio of flavones and polysaccharides in the formulation.

The section below is a summary of *Epimedium* extraction procedure and its applications in treatment of benign prostatic hyperplasia. Also, a procedure of preparing compounded formulation of *Epimedium* extract, ginseng extract, pollen and pollen extract, Radix *Astragali* extract and Cortex *Phellodendri* extract and its application in treating prostatic hyperplasia associated with chronic prostatitis are stated as follow.

Practical Cases

Case 1 Determine the Content of Flavones and Polysaccharides in Different Species of *Epimedium* Herbs.

*Epimedium* Herb is the dried aerial part of *Epimedium brevicornum, Epimedium sagittatum, Epimedium pubescens, Epimedium wushanense* or *Epimedium koreanum*. The herb is collected from Shanxi, Sichuan, Hunan, Hubei, Guizhou and Liaoning provinces. Total flavones are determined by UV spectrophotometry; icariin and icariin I are assayed by high performance liquid chromatography and polysaccharides are assayed by phenol-sulfuric acid method.

The results of these assays showed that the contents of total flavones and total polysaccharides content are 6-20% and 13-26%, respectively.

| Name of species | Sources | Content (%) | | | |
|---|---|---|---|---|---|
| | | Icariin | Icariin I | Flavones | Polysaccharides |
| Epimedium brevicornum | Shanxi | 1.193 | 0.445 | 12.3 | 20.7 |
| | Sichuan | 1.088 | 0.794 | 11.6 | 19.0 |
| Epimedium sagittatum | Hunan | 0.961 | 0.190 | 7.2 | 15.9 |
| | Hubei | 0.735 | 0.110 | 6.4 | 13.4 |
| | Guizhou | 3.098 | 0.084 | 18.3 | 26.1 |
| Epimedium wushanense | Sichuan | 3.343 | 0.094 | 20.1 | 25.6 |
| | Guizhou | 2.882 | 0.030 | 8.9 | 20.1 |
| Epimedium pubescens | Sichuan | 1.140 | 0.067 | 10.2 | 18.6 |
| Epimedium koreanum | Liaoning | 0.890 | 0.104 | 16.9 | 22.5 |

Case 2 Extraction of *Epimedium* Species

Extract 500 g *Epimedium brevicornum* (Shanxi) with 3 liters of 60% ethanol 3 times at 60° C. The extraction time is 2 hours. Filter the extract by suction filtration, recover ethanol from the eluent and add onto a resin column (D101 or D140 column, 1000 g wet weight). Wash the resin with 3 L water, and then elute with 30-85% ethanol. Recover the ethanol by suction method and evaporate to dryness. The dry weight of extract (A) is about 20 g and contains 45.8% flavones, which are predominately icariin and icariin I. The total yield is about 3%. Decoct herbal residue with 3 L water for 50 minutes and extract 3 times. Filter the aqueous solution. Concentrate the aqueous solution to 1 L and filter again. Add 95% ethanol to the concentrated extract and make up with sufficient ethanol to obtain a concentration of 75%. Mix thoroughly and stand still for 12 hour. Recover the precipitate by filtration. Dissolve the precipitate in water and precipitate with 75% ethanol again. Repeat this precipitation once more. A reddish brown polysaccharide (56 g) is obtained. Dissolve the polysaccharides in 500 ml water and mix with 100 ml chloroform n-butanol mixture (5:1). Sonicate to remove protein debris. Exclude particle with molecular weight less than 1000 Daltons by ultra filtration. Concentrate the extract and evaporate to dryness to obtain *Epimedium* polysaccharide of 36.5 g (B). The molecular weights of these polysaccharides should be in the range of 1000 to 700,000. The polysaccharides undergo routine testing and two fractions are identified—extracellular polymer substances 1 (EPS-1) and extracellular polymer substances 2 (EPS-2) with their respective molecular weights of 45000 and 620000. The composition of both EPSs is fucose, rhamnose, pentosidine, xylitose, mannitose, glucose and galactose. Furthermore, we have identified four groups of polysaccharides with their respective molecular weights of 3400, 25000, 45000 and 520000.

The *Epimedium* extracts compose of mixing A and B in the following proportions as 2:8, 3:7, 4:6 5:5, 6:4, 7:3 and 8:2.

*Epimedium* extracts are prepared from the dried aerial part of *Epimedium brevicornum, Epimedium sagittatum, Epimedium pubescens, Epimedium wushanense* or *Epimedium koreanum*. 500 g of herb to be extracted in accordance with the method mentioned above. The content of flavones is about 20-90%. The yield of each species is as follow:

| Name | Origin | Yield of A | Yield of B |
|---|---|---|---|
| *Epimedium brevicornum* | Shanxi | 20 g, 4% | 37 g, 7.4% |
|  | Sichuan | 10 g, 3% | 29 g, 5.8% |
| *Epimedium sagittatum* | Hunan | 12 g, 2.4% | 20 g, 4.0% |
|  | Hubei | 8 g, 1.6% | 30 g, 6.0% |
|  | Guizhou | 27 g, 5.8% | 39 g, 7.8% |
| *Epimedium wushanense* | Sichuan | 23 g, 4.6% | 42 g, 8.4% |
|  | Guizhou | 16 g, 3.2% | 32 g, 6.4% |
| *Epimedium pubescens* | Sichuan | 9 g, 1.8% | 25 g, 5.0% |
| *Epimedium koreanum* | Liaoning | 18 g, 3.6% | 28 g, 5.6% |

Case 3 Preparation of Compounded Formulation Containing *Epimedium* Extract with Ginseng, Pollen, Radix *Astragali* and Cortex *Phellodendri*

This Compounded Formulation is Composed of Five Herbal Extract:

The ratio of extract of *Epimedium* extract (Flavones 40%, icariin 20%,. polysaccharides 40%): ginseng extract (ginsenoside 6-10%): Pollen or pollen extract (flavones 10-20%): Radix *Astragli* extract (*Astragloside*>3-5%, Radix *Astragli* polysaccharides 20-30%): Cortex *Phellodendri* extract (berberine 10-15%) is 5:1:2:1:1.

The *Epimedium* extract is prepared according to the method described in Case 2. The ginseng extract (ginsenoside 6-10%) is prepared as follow: Extract 500 g of ginseng powder with 1-2 L 70% ethanol. Heat and reflux 2-3 times. Recover the ethanol extract by suction method. Filter and evaporate the filtrate to dryness to obtain 160 g of ginseng dry extract.

The pollen or pollen extract (flavones 10-20%) is prepared as follow: Extract 500 g of pollen with 1-2 L 75% ethanol. Heat and reflux 2-3 times. Recover the ethanol by suction method. Filter and evaporate the filtrate to dryness to obtain 126 g of pollen dry extract.

The Radix *Astragali* extract (*Astragloside*>3-5%, Radix *Astiagli* polysaccharides 20-30%) is prepared as follow:

Extract 500 g Radix *Astragali* powder with 2-4 L 75% ethanol. Heat and reflux 2-3 times. Recover the ethanol under reduced pressure. Add the filtrate onto a resin column ($D_{101}$, 1 kg) and wash the resin with water. Elute the resin with 30-85% ethanol. Concentrate and evaporate to dryness to obtain 67 g dry extract (Radix *Astragali* saponin 4.7%). Decoct the Radix *Astragli* residue with 1 L water for 3 times. Filter the extract and concentrate to 1 L. Add ethanol to make up a final concentration of 75-85% ethanol. Recover the precipitate, polysaccharide extract. Mix the saponin and polysaccharide in a radio of 3:7 to obtain Radix *Astragali* extract.

The Cortex *Phellodendri* extract (berberine 10-15%) is prepared as follow:

Extract 500 g Cortex *Phellodendri* powder with 1-2 L 75% ethanol. Heat and reflux 2-3 times. Recover the ethanol under reduced pressure. Filter and evaporate the filtrate to dryness to obtain 96 g Cortex *Phellodendri* dry extract.

Case 4 Acute Toxicology Study

*Epimedium* extract:

40 SD mice (from Kunming) that weighed 20±2 g and were in equal gender number were selected. They were fasted but were free to drink water for 16 hours before the experiment. They were divided into 2 groups (n=20). The first group mice were taken 6 g/kg *Epimedium* extract I (The A and B ratio of extract is 4:6 and the mixture contains flavones 40%, icariin 10% and polysaccharides 60%.) in single dose. The second group mice were taken 9 g/kg *Epimedium* extract I in single dose. After treatment, both groups were subjected to 7 days observations that included appetite, movement, faeces, growth and death. In other experiments with the same setting and dose given, we observed the acute toxicity of mice after they were taken *Epimedium* extract II (The A and B ratio of extract is 6:4 and the mixture contains flavones 40%, icariin 20% and polysaccharides 40%.), *Epimedium* extract III (The A and B ratio of extract is 7:3 and the mixture contains icariin 60% and polysaccharides 30%.) or the compounded formulation described in Case 3 (*Epimedium* species, ginseng, pollen, Radix *Astragli* and Cortex *Phellodendri*).

The results concluded that oral dose of the $LD_{50}$ of *Epimedium* extract I, *Epimedium* extract II, *Epimedium* extract III and the compounded formulation could not be determined. Therefore the oral dose of $LD_{50}$ is greater than 9 g/kg.

Case 5 Results of Clinical Research

1. The Objectives of Clinical Research;
1) Observe the efficacy of *Epimedium* extract in treatment of benign prostatic hyperplasia (BPH) and its adverse effects;
2) Observe the efficacy of the compounded formulation in Case 3 in treatment of BPH associated with chronic prostatitis and its adverse effects;

2. The Criteria of Patient Selection;
1) Patients who suffer from BPH and age>50;
2) Patients who suffer from BPH and prostatitis, and age>30;
3) Patients who have a symptomatic score ≧6, and associates with abnormal biochemical assays;
4) Patients who suffer from BPH, erectile dysfunction and early ejaculations.

Patient Statistical Information:

| Group | Number of patients | Age (Year) | Duration of illness (Year) |
|---|---|---|---|
| Benign prostatic hyperplasia* | 32 | 64.90 ± 7.8 | 11.5 ± 8.7 |
| BPH and chronic prostatitis** | 24 | 42.42 ± 12.1 | 3.5 ± 3.3 |

*Benign prostatic hyperplasia group is taken *Epimedium* extract;
**BPH and chronic prostatitis group all associated with sexual dysfunction is taken the *Epimedium* compounded formulation (with ginseng, pollen, Radix *Astragli* and Cortex Phellodendri)

3. Treatment

Benign prostatic hyperplasia group: Dosage of *Epimedium* extract (The A and B ratio of extract is 6:4 and the mixture contains flavones 40%, icariin 20% and polysaccharides 40%): 250 mg/cap×3 caps twice daily.

BPH and chronic prostatitis group: Dosage of Compounded formulation described in Case 3: 250 mg/cap×3 caps twice daily.

4. Observation Criteria: Subjects with an Accumulative Score Higher than 6 are Selected. The Scoring System is Listed as Follow:

Clinical symptomatic scores for benign prostatic hyperplasia

| Symptoms | 0 | 1 | 2 | 3 |
|---|---|---|---|---|
| Urine excretion | Normal | Small volume or linear | Urine flow broken but still linear | Urine flow in droplet and non-linear |
| Abdominal symptoms | None | Urge to urination | Bloating | Bloating and pain |
| Time of urination | <40 s | 40–50 s | 51–60 s | >60 s |
| Rate of urine flow | >15 ml/s | 11–15 ml/s | 6–10 ml/s | <6 ml/s |
| Urine retention | 10 ml | 10–50 ml | 50–100 ml | >100 ml |
| Prostatic hyperplasia | Normal | Hyperplasia I | Hyperplasia II | Hyperplasia III |

Note:
The stage of benign prostatic hyperplasia, reference: Sex hormone and geriatric illness, the 1st edition. Beijing: Chinese scientific technological Publisher 1998. 171–189

5. Standard of Clinical Efficacy

Clinically cure: Main symptoms disappear; accumulative score is reduced more than 90%; biochemical index-returns normal.

Excellent effect: Major symptoms disappear; accumulative score is reduced by 60-89%; biochemical index basically returns normal.

Improvement: Major symptoms reduce or disappear; the score is reduced by 15-59%; biochemical index improves.

No effect: Major symptoms do not change or even worsen.

6. Observation of Adverse Effects:

Hematology: Changes in RBC, Hb, WBC and Plt before and after treatment.

Urine test: Changes in proteinuria and RBC before and after treatment.

Liver function: Changes in ALT and AST before and after treatment.

Renal function: Changes in BUN and Cr before and after treatment.

7. Statistical Method:

Quantitative data would be shown in a form of X±SD, compared with t-test; Ridit is used for group data processing.

8. Results:

1) Comparison of accumulative clinical symptom scores between BPH and BPH associated with chronic prostatitis group before and after treatment are listed in the following table.

TABLE 1

Comparison the accumulative clinical symptom scores between two treatment groups (X ± SD)

| Group | Score before treatment | Score after treatment | P value |
|---|---|---|---|
| BPH | 12.16 ± 2.42 | 6.26 ± 1.98 | $P < 0.01$ |
| BPH associated with chronic prostatitis | 10.42 ± 2.54 | 4.88 ± 2.82 | $P < 0.01$ |

2) Urine retention. The symptom of urine retention in both groups is significantly reduced after treatment.

TABLE 2

Comparison of urine retention between two treatment groups (unit: ml, X ± SD)

| Group | Volume before treatment | Volume after treatment | P value |
|---|---|---|---|
| BPH | 65.93 ± 60.19 | 37.19 ± 43.05 | $P < 0.05$ |
| BPH associated with chronic prostatitis | 45.83 ± 53.48 | 25.41 ± 34.38 | $P < 0.05$ |

3) Urine flow rate. The rate of urine flow in both groups is significantly increased after treatment.

TABLE 3

Comparison of urine flow rate between two treatment groups (unit: ml/s, X ± SD)

| Group | Flow rate before treatment | Flow rate after treatment | P value |
|---|---|---|---|
| BPH | 4.41 ± 1.44 | 7.74 ± 3.33 | $P < 0.01$ |
| BPH associated with chronic prostatitis | 7.02 ± 3.29 | 10.91 ± 5.46 | $P < 0.01$ |

4) Prostate Specific Antigen (PSA) assay. BPH associated with chronic prostatitis group showed a significant decrease in PSA.

TABLE 4

Comparison of PSA level between two treatment groups (unit: ug/L, X ± SD)

| Group | PSA before treatment | PSA after treatment | P value |
|---|---|---|---|
| BPH | 3.31 ± 3.68 | 3.03 ± 3.84 | $P > 0.05$ |
| BPH associated with chronic prostatitis | 4.41 ± 5.28 | 1.84 ± 1.07 | $P < 0.01$ |

5) The overall effectiveness of treatment between benign prostatic hyperplasia group and benign prostatic hyperplasia associated with chronic prostatitis group.

TABLE 5

Comparison of overall efficacy between two treatment groups

| | Group | |
|---|---|---|
| | BPH | BPH associated with chronic prostatitis |
| Number of patient | 32 | 24 |
| Clinically cure | 2 | 1 |
| Excellent effect | 12 | 6 |
| Improvement | 16 | 11 |

TABLE 5-continued

Comparison of overall efficacy between two treatment groups

| | Group | |
|---|---|---|
| | BPH | BPH associated with chronic prostatitis |
| No effect | 2 | 6 |
| Total effective patients | 30 | 18 |
| Total effective rate | 93.8% | 75.0% |

Ridit is used for data analysis between two groups. The result is P<0.05, which can be shown that towards BPH group improved more significant than that of BPH associated with chronic prostatitis.

The overall review in the treatment of sexual dysfunction in BPH and BPH associated with chronic prostatitis group: Patients in both groups were taken the compounded formulation described in Case 3 with regimen of 250 mg/cap×3 caps twice daily. The overall improvement was 28.6% in patients suffered from erectile dysfunction and 50% in patients suffered from early ejaculation.

This clinical study showed that *Epimedium* extract is effective in BPH with a success rate of 93.8%. This patient group's symptomatic score decreases significantly (P<0.01) and their quality of life improves prominently, which can be seen from the reduced frequency in nocturnal urination and improvement in urine flow. The rate of urine flow increases substantially (P<0.01), which implies a decrease in bladder obstruction. Moreover, the urine retention is decreased (P<0.01). The level of Prostate Specific Antigen (PSA) decreased after treatment from a value of 3.31±3.68 ug/L (before treatment) to 3.03±3.84 ug/L (after treatment), but this result is not statistically significant.

This clinical study also showed that the formulation of *Epimedium* extract, pollen or pollen extract, Radix *Astragli* extract, Cortex *Phellodendri* extract and ginseng extract is effective in treating patients with BPH associated with chronic prostatitis and its success rate is 75%. This patient group's symptomatic score decreases significantly (P<0.01) and their quality of life improves prominently, which can be seen from the reduced frequency in nocturnal urination and improvement in urine flow. The rate of urine flow increases substantially (P<0.01), which implies a decrease in bladder obstruction. Moreover, the urine retention is decreased (P<0.01). The level of PSA decreases significantly after treatment from a value of 4.41±5.28 ug/L (before treatment) to 1.84±1.07 ug/L (after treatment), with a P value <0.01. The rates of improvement in symptoms of erectile dysfunction and early ejaculation were 28.6% and 50.0%, respectively.

In this clinical study, patients experience no adverse effects. The hematological test, liver function, renal function and urine test are normal before and after treatment.

The *Epimedium* extract contains well-defined active components. This invention provides a simple procedure to prepare *Epimedium* extract, which is suitable for industrial manufacturing. Moreover, *Epimedium* extract is demonstrated clinically effective in patients with benign prostatic hyperplasia.

What is claimed is:

1. A pharmaceutical composition used in treatment of prostatic hyperplasia and prostatitis, wherein the pharmaceutical composition comprises: Radix Ginseng extract pollen or pollen extract or both pollen and pollen extract, Radix Astragali extract, Cortex Phellodendri extract, and *Epimedium* extract which comprises *Epimedium* crude flavones and *Epimedium* polysaccharides in a ratio of from 2:8 to 8:2 by weight of the *Epimedium* extract, and wherein the *Epimedium* extract is free of polysaccharides having a molecular weight below 1,000 Daltons.

2. The composition of claim 1, comprising:
   a. 1-6 parts by weight of the Radix Ginseng extract, containing 6-10% ginsenoside by weight of the Radix Ginseng extract;
   b. 1-8 parts by weight of pollen or pollen extract or both, containing 10-20% flavones by weight of the pollen or pollen extract or both;
   c. 1-4 parts by weight of the Radix Astragali extract, containing 3-5% astragaloside and 20-30% polysaccharides by weight of the Radix Astragali extract;
   d. 1-6 parts by weight of the Cortex Phellodendri extract, containing 10-15% berberine by weight of the Cortex Phellodendri extract; and
   e. 4-16 parts by weight of *Epimedium* extract containing 20-90% flavones by weight of the crude flavones, and the *Epimedium* polysaccharide, and
   wherein the parts by weight are based on the total parts by weight of the composition.

3. The composition of claim 2, wherein the composition comprises by weight: 1-2 parts portion of Ginseng extract, 2-4 parts of the pollen or pollen extract or both, 1-2 parts of the Radix Astragali extract, 1-2 parts of Cortex Phellodendri extract and 5-10 parts of the *Epimedium* extract comprising the crude flavones and the *Epimedium* polysaccharides.

4. The pharmaceutical composition of claim 1, further comprising one or more pharmaceutically acceptable vehicle/excipients to formulate various preparations in different dosage forms.

5. The pharmaceutical composition of claim 2, further comprising one or more pharmaceutically acceptable vehicle/excipients to formulate various preparations in different dosage forms.

6. The pharmaceutical composition of claim 3, further comprising one or more pharmaceutically acceptable vehicle/excipients to formulate various preparations in different dosage forms.

* * * * *